United States Patent
Catinat et al.

(10) Patent No.: US 8,058,459 B2
(45) Date of Patent: *Nov. 15, 2011

(54) PROCESS FOR THE MANUFACTURE OF 1,2-EPOXY-3-CHLOROPROPANE

(75) Inventors: Jean-Pierre Catinat, Waudrez (BE); Michel Strebelle, Brussels (BE)

(73) Assignee: Solvay (SociétéAnonyme), Brussels (BE)

( * ) Notice: Subject to any disclaimer, the term of this patent is extended or adjusted under 35 U.S.C. 154(b) by 1249 days.

This patent is subject to a terminal disclaimer.

(21) Appl. No.: 10/534,502

(22) PCT Filed: Nov. 10, 2003

(86) PCT No.: PCT/EP03/12506
§ 371 (c)(1), (2), (4) Date: Sep. 19, 2005

(87) PCT Pub. No.: WO2004/048353
PCT Pub. Date: Jun. 10, 2004

(65) Prior Publication Data
US 2006/0041150 A1    Feb. 23, 2006

(30) Foreign Application Priority Data
Nov. 12, 2002 (FR) ...................... 02 14207

(51) Int. Cl.
*C07D 301/12* (2006.01)
(52) U.S. Cl. ...................................... 549/531
(58) Field of Classification Search .............. 549/531
See application file for complete search history.

(56) References Cited

U.S. PATENT DOCUMENTS

| | | | |
|---|---|---|---|
| 6,063,941 A * | 5/2000 | Gilbeau | 549/518 |
| 6,288,248 B1 * | 9/2001 | Strebelle et al. | 549/518 |
| 6,350,888 B1 | 2/2002 | Strebelle et al. | |
| 2004/0068127 A1 | 4/2004 | Schoebrechts et al. | |
| 2005/0054864 A1 | 3/2005 | Strebelle et al. | |
| 2006/0167288 A1 * | 7/2006 | Strebelle et al. | 549/531 |

FOREIGN PATENT DOCUMENTS

| | | | |
|---|---|---|---|
| EP | 1 072 600 | | 1/2001 |
| EP | 1 085 017 | | 3/2001 |
| JP | 04327582 A | * | 11/1992 |
| WO | 96/03362 | | 2/1996 |
| WO | WO 96/03362 | * | 8/1996 |
| WO | 99/24164 | | 5/1999 |
| WO | 99/28029 | | 6/1999 |
| WO | 99/48882 | | 9/1999 |

OTHER PUBLICATIONS

Carlo Venturello: "A New, Effective Catalytic System for Epoxidation of Olefins by Hydrogen Peroxide under Phase-Transfer Conditions." J. Org. Chem., vol. 48, No. 21, pp. 3831-3833, 1983. XP001012726.

Carlo Venturello: "Quaternary Ammonium Tetrakis(diperoxotungsto)phosphates(3-) as a New Class of Catalysts for Efficient Alkene Epoxidation with Hydrogen Peroxide" J. Org. Chem., vol. 53, No. 7, pp. 1553-1557, 1988. XP002235620.

* cited by examiner

*Primary Examiner* — Janet Andres
*Assistant Examiner* — John Mabry
(74) *Attorney, Agent, or Firm* — Oblon, Spivak, McClelland, Maier & Neustadt, L.L.P.

(57) ABSTRACT

Process for the manufacture of 1,2-epoxy-3-chloropropane by reaction between allyl chloride and hydrogen peroxide in the presence of a catalyst and in the possible presence of at least one solvent in an epoxidation medium comprising at least one liquid phase, in which process the pH of the liquid phase is controlled and maintained at a value of greater than or equal to 1.5 and less than 4.8.

16 Claims, No Drawings

PROCESS FOR THE MANUFACTURE OF 1,2-EPOXY-3-CHLOROPROPANE

The invention relates to a process for the manufacture of 1,2-epoxy-3-chloropropane by reaction between allyl chloride and hydrogen peroxide.

It is known to manufacture 1,2-epoxy-3-chloropropane (or epichlorohydrin) by epoxidation of allyl chloride by means of hydrogen peroxide in the presence of methanol as solvent and in the presence of a catalyst comprising TS-1, as disclosed in U.S. Pat. No. 6,350,888.

This known process, without control of the pH of the epoxidation medium, exhibits the disadvantage of poor selectivity of the epoxidation reaction and consequently significant formation of undesirable byproducts.

The present invention is targeted at overcoming this disadvantage by providing a novel process in which the formation of byproducts is greatly reduced without, however, reducing the activity of the catalyst (or the degree of conversion of the reactants, or the rate of the epoxidation reaction). The byproducts which can be formed are, for example, the result of the methanolysis of epichlorohydrin to chloromethoxypropanols or of the hydrolysis to chloropropanediol.

The invention consequently relates to a process for the manufacture of 1,2-epoxy-3-chloropropane by reaction between allyl chloride and hydrogen peroxide in the presence of a catalyst and in the possible presence of at least one solvent in an epoxidation medium comprising at least one liquid phase, in which process the pH of the liquid phase is controlled and maintained at a value of greater than or equal to 1.5 and less than 4.8.

The term "control of the pH" is understood to mean the periodic or continuous measurement of the pH during the process, so as to monitor its change throughout the process and thus to be able to act, when the pH becomes too high or too low, in order to prevent the pH from reaching a value of greater than or equal to 4.8 or less than 1.5.

One of the essential characteristics of the invention lies in the control of the pH of the liquid phase of the epoxidation medium. This is because it has been found that, when the pH is controlled and maintained at a value of greater than or equal to 1.5 and less than 4.8, the advantage is observed, in comparison with a process carried out without control of the pH, that the selectivity of the epoxidation is higher without excessively reducing the activity of the catalyst.

Without being committed to a scientific theory, the Applicant Company believes that the pH has an influence on the selectivity of the epoxidation reaction. This might be explained by the fact that an excessively high pH would inhibit the activity of the catalyst while an excessively acidic pH would favour the formation of byproducts.

In the process according to the invention, the pH of the liquid phase of the epoxidation medium can be controlled and measured by any appropriate known means. When the pH is measured at ambient temperature with a Metrohm® 6.0239.100 electrode (electrolyte 3M KCl) on a withdrawn sample of the epoxidation medium, it has to be controlled so as to maintain it at a value of greater than or equal to 1.5 and less than 4.8. Generally, the pH is maintained at a value of greater than or equal to 1.75, in particular of greater than or equal to 2, more particularly of greater than or equal to 2.5, the values greater than or equal to 3 giving satisfactory results. The pH is advantageously maintained at a value of less than or equal to 4.5, more especially of less than or equal to 4.2, the values of less than or equal to 4 giving good results.

The pH can be modified by addition of a base or of a mixture of a salt and its acid or of its conjugate base. The base can be chosen from water-soluble bases. They can be strong bases or weak bases. Mention may be made, as examples, of an alkali metal or alkaline earth metal hydroxide, carbonate or acetate. Sodium hydroxide is preferred.

The term "epoxidation medium" in which the epoxidation reaction of the process according to the invention takes place is understood to mean a medium comprising at least one liquid phase, comprising allyl chloride, hydrogen peroxide, if appropriate the solvent, the 1,2-epoxy-3-chloropropane formed and optionally byproducts, and a solid phase comprising the catalyst. The liquid phase of the epoxidation medium also generally comprises water, typically in a concentration of 5 to 25% by weight.

The epoxidation medium can also comprise two liquid phases, a first liquid phase, essentially aqueous, comprising the hydrogen peroxide and at least a portion of the solvent, if appropriate, and a second liquid phase, essentially organic, comprising allyl chloride, the 1,2-epoxy-3-chloropropane formed, optionally byproducts and at least one other portion of the solvent, if appropriate. The epoxidation medium may be devoid of solvent.

When the epoxidation medium comprises two liquid phases, the pH is measured as described above but with vigorous stirring of the two liquid phases, so as to obtain a constant and reproducible pH measurement throughout the stirred medium.

The process according to the invention makes it possible to obtain selectivities which are generally greater than or equal to 95 mol % for epichlorohydrin, calculated as in the examples described later, in particular greater than or equal to 96%. The selectivity is usually less than or equal to 99.5%, more especially less than or equal to 99%.

In the process according to the invention, it may furthermore prove to be advantageous to employ an allyl chloride purified so that it comprises less than 2000 ppm of 1,5-hexadiene. This is because it has been found that the use of purified allyl chloride makes it possible to increase the duration of use of the catalyst (and thus to reduce the frequency with which the catalyst has to be removed from the epoxidation medium in order to be replaced or to be regenerated) while retaining a high activity and a high selectivity.

The purified allyl chloride can be obtained by any appropriate known means, for example by chlorination, as disclosed in International Application WO 96/03362. The purification can also be carried out by distillation.

The purified allyl chloride generally comprises an amount of 1,5-hexadiene of less than 1000 ppm by weight and preferably of less than or equal to 500 ppm by weight; values of less than or equal to 400 ppm by weight and in particular of less than or equal to 300 ppm are the most advantageous. The amount of 1,5-hexadiene present in the purified allyl chloride is usually greater than or equal to 1 ppm by weight, generally greater than or equal to 10 ppm by weight.

In the process according to the invention, the hydrogen peroxide is advantageously employed in the form of an aqueous solution. The aqueous solution generally comprises at least 10% by weight of hydrogen peroxide, in particular at least 20% by weight. It usually comprises at most 70% by weight of hydrogen peroxide, in particular 50% by weight.

Generally, the molar ratio of the amount of allyl chloride employed to the amount of hydrogen peroxide employed is greater than or equal to 0.1, in particular greater than or equal to 0.5 and preferably greater than or equal to 1. This ratio is usually less than or equal to 100, more especially less than or equal to 50, generally less than or equal to 25. In a particularly advantageous alternative form of the process according to the invention, use is made of an excess of allyl chloride so that the molar ratio of the amount of allyl chloride employed to the amount of hydrogen peroxide employed is greater than or equal to 2, in particular greater than or equal to 3, very particularly greater than or equal to 4. In this advantageous alternative form, the ratio is generally less than or equal to 10, more especially less than or equal to 8 and usually less than or equal to 7. A ratio of approximately 5 is particularly well suited. The use of an excess of allyl chloride in this alternative form makes it possible to obtain an even greater increase in the selectivity and, in combination with the purified allyl chloride, makes it possible to also obtain a reduction in the deactivation of the catalyst.

The solvent optionally used in the process according to the invention can be chosen from any organic solvent which is at least partially soluble in water, and their mixtures. Solvents which are particularly suitable are alcohols. The preferred alcohols comprise from 1 to 5 carbon atoms. Those which comprise a single —OH group are highly suitable. Mention may be made, as examples, of methanol, ethanol, n-propanol, isopropanol, butanol and pentanol. Generally, it is methanol or tert-butanol. Methanol is the commonest.

When the epoxidation medium comprises only a single liquid phase, the latter generally comprises at least 30% by weight of solvent, in particular at least 50% by weight. This amount is usually at most 90% by weight, more especially at most 75% by weight When the epoxidation medium comprises two liquid phases, the epoxidation medium can comprise less solvent and may even be devoid of solvent.

The catalyst used in the process according to the invention generally comprises a zeolite, namely a solid comprising silica which exhibits a microporous crystalline structure. The zeolite is advantageously devoid of aluminium. It preferably comprises titanium.

The zeolite which can be used in the process according to the invention can have a crystalline structure of ZSM-5, ZSM-11 or MCM-41 type or of zeolite beta type. Zeolites of ZSM-5 type are highly suitable. Those exhibiting an infrared absorption band at approximately 950-960 $cm^{-1}$ are preferred.

The zeolites which are particularly well suited are the titanium silicalites. Those corresponding to the formula $xTiO_2(1-x)SiO_2$ in which x is from 0.0001 to 0.5, preferably from 0.001 to 0.05, and exhibiting a crystalline structure of ZSM-5 type give particularly favourable results.

The catalyst is advantageously provided in the form of spherical particles obtained by any known method. A method which is particularly well suited is that disclosed in International Application WO 99/24164 from Solvay (Société Anonyme). The catalyst can also be provided in the form of non-spherical particles obtained, for example, by extrusion as disclosed in International Application WO 99/28029 from Solvay (Société Anonyme).

The catalyst particles generally exhibit a mean diameter of greater than or equal to 0.01 mm and less than or equal to 5 mm, a specific surface of greater than or equal to 1 $m^2/g$ and less than or equal to 900 $m^2/g$ (determined according to the nitrogen adsorption method), a bulk density of between 0.1 and 1.0 g/ml, a pore volume of between 0.25 and 2.5 ml/g and a distribution of the diameters of the pores with a maximum of between 15 and 2000 Å.

The catalyst can be present in the process according to the invention in the form of a bed. It can be a stationary bed or a fluid bed. A fluid bed is preferred.

The epoxidation reaction of the process according to the invention can be carried out in any type of appropriate reactor. It can, for example, be a single-pass bed. It can also be a reactor of loop type comprising recirculation of the epoxidation medium, with or without recirculation of the catalyst.

The temperature at which the epoxidation reaction can be carried out is generally greater than or equal to 0° C., in particular greater than or equal to 35° C., more particularly greater than or equal to 45° C. and preferably greater than or equal to 55° C. The temperature is usually less than or equal to 120° C., more especially less than or equal to 100° C., generally less than or equal to 80° C., temperatures of less than or equal to 65° C. giving highly satisfactory results. When the temperature is from 45 to 80° C., the advantage is observed, in comparison with a lower temperature, for example of approximately 35° C., that the rate of deactivation of the catalyst is reduced.

The process of the invention can be carried out at any pressure at least equal to the vapour pressure of the constituents of the epoxidation medium.

The process according to the invention can be carried out continuously or batchwise.

EXAMPLES

The tests were carried out in a plant composed essentially of a tubular reactor, jacketed under pressure, in a liquid-solid fluidized bed (diam.: 1.5 cm, h: 50 cm), with a recirculation loop. The loop comprises in particular a reflux condenser, at atmospheric pressure, positioned directly at the outlet of the reactor (condensation of the allyl chloride), and a pH probe, making it possible to regulate the pH. The overall volume of the plant was approximately 350 ml.

The temperature of the reactor was regulated using a cryothermostat.

The pressure in the reactor was regulated at 4.5 bar using a pneumatic valve.

The epoxidation medium was reduced in pressure from its exit from the reactor and the liquid-gas mixture resulting therefrom was cooled by passing into a jacketed glass coil. The set point of the cryothermostat was fixed at −20° C.

The liquid phase was divided into two streams at the outlet of the condenser:

the liquid outflow, the flow rate of which corresponded to that of the reactant feeds, and a second greater outflow, which formed the recirculation shuttle. The $H_2O_2$, allyl chloride (ALC) and methanol ($CH_3OH$) feeds were added to this recirculation stream. It is also at this level that the system for measuring and regulating the pH was situated.

Movement towards the reactor was provided using a membrane pump. The recirculation flow rate was measured using a flow meter and was adjusted to 5 l/h. Before entering the reactor, the liquid passed through a preheater.

Use was made, in these tests, of 18.6 g of a catalyst (i.e. 6.5 g TS-1) provided in the form of 0.4-0.6 mm beads composed of Ti silicalite (35 weight %) dispersed in a microporous silica matrix (65 weight %). They are prepared according to a sol-gel process in the presence of a gas phase (as disclosed in WO 99/24164 from Solvay (Société Anonyme)).

The feed flow rates corresponding to the two types of epoxidation medium used are shown below.

Epoxidation Medium 1:
  ALC/$H_2O_2$: 2 mol/mol
  MeOH/ALC: 7.8 mol/mol
  ALC: 38.2 ml/h
  MeOH: 148.2 ml/h
  39 weight % $H_2O_2$: 20.5 g/h Epoxidation Medium 2:
  ALC/$H_2O_2$: 5 mol/mol
  MeOH/ALC: 2.1 mol/mol
  ALC: 95.5 ml/h
  MeOH: 99.7 ml/h
  39 weight % $H_2O_2$: 20.5 g/h The degree of conversion (DC) of the $H_2O_2$ was calculated from the inlet and outlet flow rates of the $H_2O_2$, the latter being determined using the results of the iodometric assay of the residual $H_2O_2$ in the overflow liquid:

DC (%)=100×($H_2O_2$ employed in mol/h−unconverted $H_2O_2$ in mol/h)/$H_2O_2$ employed in mol/h with unconverted $H_2O_2$=concentration of $H_2O_2$ in the overflow in mol/kg×overflow flow rate in kg/h.

The term "C3 formed" is understood to mean epichlorohydrin (EPI) and the various byproducts resulting from the opening of the oxirane ring, namely 1-chloro-3-methoxy-2-propanol (recorded as 1C3OMe2Pol), 1-chloro-2-methoxy-3-propanol (recorded as 1C2OMe3Pol), 3-chloro-1,3-propanediol (recorded as MCG) and 1,3-dichloro-2-propanol (recorded as 1,3DCPol).

The EPI/C3 formed selectivity can thus be calculated, from the chromatogram obtained by vapour-phase chromatography of the liquid outflow, using the expression:

EPI/C3f selectivity (%)=100×EPI$_{formed}$ in mol/h/Σ (EPI+1C3OMe2Pol+1C2OMe3Pol+MCG+1,3DCPol)$_{formed}$ in mol/h.

The pH of the liquid outflow was measured periodically off-line. To do this, use was made of a titroprocessor (682 Titroprocessor, Metrohm®) and a combined pH electrode (6.0239.100 from Metrohm®). This electrode, the electrolyte of which is 3M KCl, was calibrated daily using two aqueous buffer solutions of pH 7 and 4.

Examples 1 (In Accordance with the Invention) and 2 (Not in Accordance with the Invention)

Example 1, with regulation of the pH, was carried out under the following conditions: 55° C., "high purity" ALC (comprising 180 ppm by weight of 1,5-hexadiene), ALC/$H_2O_2$ ratio of 5 mol/mol and $CH_3OH$/ALC ratio of 2.1 mol/mol. The pH was regulated at a value of 3.5 using a 0.1 molar solution of NaOH in a 1:1 (vol/vol) $H_2O$/$CH_3OH$ mixture, the presence of $CH_3OH$ being necessary to make it possible to avoid possible segregation in the event of addition of significant amounts of base.

The comparison with Example 2, carried out without pH regulation, clearly indicates that the conversion is only slightly affected by the pH regulation, at least under the conditions used here: the difference in conversion does not exceed 2 to 3%. In contrast, the EPI/C3 formed selectivities are quite markedly superior to those measured in the absence of regulation.

The results are given in Table 1.

TABLE 1

| Time (h) | | Example 1 With regulation | Example 2 Without regulation |
|---|---|---|---|
| 25 | Conversion (%) | 95.3 | 96.9 |
|  | EPI/C3f selectivity (%) | 96.9 | 93.7 |
| 50 | Conversion (%) | 89.3 | 92.1 |
|  | EPI/C3f selectivity (%) | 97.2 | 94.3 |
| 78 | Conversion (%) | 83.3 | 85.1 |
|  | EPI/C3f selectivity (%) | 97.4 | 94.4 |

Examples 3 (In Accordance with the Invention) and 4 (Not in Accordance with the Invention)

Examples 3 and 4 were carried out under the following conditions: 65° C. (Example 3) and 55° C. (Example 4), "high purity" ALC (comprising 180 ppm by weight of 1,5-hexadiene), ALC/$H_2O_2$ ratio of 5 mol/mol and $CH_3OH$/ALC ratio of 2.1 mol/mol.

In Example 3, the pH was regulated using a 0.1 molar solution of NaOH in a 1:1 (vol/vol) $H_2O$/$CH_3OH$ mixture and was maintained at a value of 3.7.

Example 4 was carried out without pH regulation.

The results are given in Table 2.

TABLE 2

|  | Example 3 T°: 65° C. With pH regulation | Example 4 T°: 55° C. Without pH regulation |
|---|---|---|
| Degree of conversion $H_2O_2$ (%) | 92.0 | 92.2 |
| EPI/C3f selectivity (%) | 96.3 | 94.4 |
| Time (h) | 195 | 53 |

The fact of increasing the temperature while regulating the pH makes it possible to combine high EPI/C3f selectivity and high $H_2O_2$ conversion and also to limit the deactivation.

Examples 5 and 6 (Not in Accordance with the Invention)

Examples 5 and 6, without regulation of the pH, were carried out under the following conditions: 35° C. (Example 5) and 55° C. (Example 6), "high purity" ALC (comprising 180 ppm by weight of 1,5-hexadiene), ALC/$H_2O_2$ ratio of 2 mol/mol and $CH_3OH$/ALC ratio of 7.8 mol/mol. The results are given in Table 3.

TABLE 3

|  | Example 5 T: 35° C. | Example 6 T: 55° C. |
|---|---|---|
| Degree of conversion $H_2O_2$ (%) | 44.7 | 42.9 |
| EPI/C3f selectivity (%) | 97.3 | 90.8 |
| Time (h) | 27 | 228 |

If the pH is not regulated, the increase in the temperature is reflected by a slower deactivation but also by a lower EPI/C3f selectivity.

The invention claimed is:

1. A process for the manufacture of 1,2-epoxy-3-chloropropane comprising reacting allyl chloride and hydrogen peroxide in an epoxidation medium comprising at least one liquid phase and in the presence of a catalyst comprising a zeolite, wherein the pH of the liquid phase is controlled and maintained at a value of greater than or equal to 1.5 and less than 4.8.

2. The process according to claim 1, wherein the pH of the liquid phase is maintained at a value from 1.75 to 4.5.

3. The process according to claim 2, wherein the pH of the liquid phase is maintained at a value from 2 to 4.2.

4. The process according to claim 1, wherein the allyl chloride comprises less than 2000 ppm of 1,5-hexadiene.

5. The process according to claim 1, wherein the reaction is carried out at a temperature from 45 to 80° C.

6. The process according to claim 1, wherein the amounts of allyl chloride and hydrogen peroxide are such that the molar ratio allyl chloride/hydrogen peroxide is from 2 to 7.

7. The process according to claim 1, wherein said epoxidation medium further comprises a solvent.

8. The process according to claim 1, wherein the catalyst comprises TS-1.

9. The process according to claim 1, wherein the catalyst is present in the form of a fluid bed.

10. The process according to claim 1, wherein the reaction is carried out in a loop reactor comprising recirculation of the epoxidation medium.

11. The process according to claim 7, wherein the solvent comprises methanol.

12. The process according to claim 1, wherein said epoxidation medium comprises a single liquid phase.

13. The process according to claim 1, wherein said epoxidation medium comprises two liquid phases.

14. The process according to claim 1, wherein said at least one liquid phase comprises water.

15. The process according to claim 12, wherein said single liquid phase comprises water.

16. The process according to claim 13, wherein a first liquid phase comprises said hydrogen peroxide and a second liquid phase comprises said allyl chloride.

* * * * *